US009326970B2

(12) United States Patent
Garner et al.

(10) Patent No.: US 9,326,970 B2
(45) Date of Patent: *May 3, 2016

(54) CHOLINE ESTERS

(71) Applicant: Encore Health, LLC, Roanoke, VA (US)

(72) Inventors: William Garner, Eastport, ME (US); Margaret Garner, Eastport, ME (US); George Minno, North Andover, MA (US); David Gooden, Durham, NC (US)

(73) Assignee: Encore Health LLC, Roanoke, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/525,471

(22) Filed: Oct. 28, 2014

(65) Prior Publication Data
US 2015/0111959 A1 Apr. 23, 2015

Related U.S. Application Data

(60) Continuation of application No. 13/851,355, filed on Mar. 27, 2013, now abandoned, which is a division of application No. 12/815,526, filed on Jun. 15, 2010, now Pat. No. 8,410,162.

(60) Provisional application No. 61/187,005, filed on Jun. 15, 2009, provisional application No. 61/224,930, filed on Jul. 13, 2009, provisional application No. 61/242,232, filed on Sep. 14, 2009.

(51) Int. Cl.
| A61K 31/385 | (2006.01) |
| A61K 9/00 | (2006.01) |
| A61K 31/21 | (2006.01) |
| C07D 339/04 | (2006.01) |
| C07D 343/00 | (2006.01) |

(52) U.S. Cl.
CPC ............ *A61K 31/385* (2013.01); *A61K 9/0048* (2013.01); *A61K 31/21* (2013.01); *C07D 339/04* (2013.01); *C07D 343/00* (2013.01)

(58) Field of Classification Search
CPC ... A61K 9/0048; A61K 31/21; A61K 31/385; C07D 343/00; C07D 339/04
See application file for complete search history.

(56) References Cited

U.S. PATENT DOCUMENTS

| 3,238,224 A | 3/1966 | Ohara et al. |
| 3,855,240 A | 12/1974 | Mueller |
| 4,210,667 A | 7/1980 | Sarges et al. |
| 4,755,528 A | 7/1988 | DuPriest et al. |
| 5,395,356 A | 3/1995 | King et al. |
| 5,459,133 A | 10/1995 | Neufeld |
| 5,465,737 A | 11/1995 | Schachar |
| 5,466,680 A | 11/1995 | Rudy |
| 5,476,515 A | 12/1995 | Kelman et al. |
| 5,488,050 A | 1/1996 | Neufeld |
| 5,503,165 A | 4/1996 | Schachar |
| 5,527,774 A | 6/1996 | Giard |
| 5,529,076 A | 6/1996 | Schachar |
| 5,624,955 A | 4/1997 | Nagasawa et al. |
| 5,665,770 A | 9/1997 | Treao et al. |
| 5,686,450 A | 11/1997 | Hellberg et al. |
| 5,688,828 A | 11/1997 | Hellberg et al. |
| 5,691,379 A | 11/1997 | Ulrich et al. |
| 5,722,952 A | 3/1998 | Schachar |
| 5,817,630 A | 10/1998 | Hofmann et al. |
| 5,843,184 A | 12/1998 | Cionni |
| 5,869,468 A | 2/1999 | Freeman |
| 5,874,455 A | 2/1999 | Terao et al. |
| 5,888,243 A | 3/1999 | Silverstrini |
| 6,007,510 A | 12/1999 | Nigam |
| 6,013,462 A | 1/2000 | Kauvar et al. |
| 6,030,950 A | 2/2000 | Ohlenschlager |
| 6,063,116 A | 5/2000 | Kelleher |
| 6,153,647 A | 11/2000 | Mallet et al. |
| 6,214,044 B1 | 4/2001 | Silverstrini |
| 6,288,106 B1 | 9/2001 | Pearson et al. |
| 6,313,164 B1 | 11/2001 | Fujita et al. |
| 6,339,102 B1 | 1/2002 | Meyerhoff et al. |
| 6,387,945 B2 | 5/2002 | Packer et al. |
| 6,472,541 B2 | 10/2002 | Tslen et al. |
| 6,664,287 B2 | 12/2003 | Avery et al. |
| 6,703,039 B2 | 3/2004 | Xia et al. |
| 6,743,779 B1 | 6/2004 | Unger et al. |
| 6,923,955 B2 | 8/2005 | Till et al. |
| 7,164,943 B2 | 1/2007 | Roy |

(Continued)

FOREIGN PATENT DOCUMENTS

| EP | 0 369 880 | 5/1990 |
| WO | WO 93/25166 | 12/1993 |
| WO | WO 93/25199 | 12/1993 |
| WO | WO 94/01773 | 1/1994 |
| WO | WO 02/13863 | 2/2002 |
| WO | WO 02/056804 | 7/2002 |
| WO | WO 03/084532 | 10/2003 |
| WO | WO 2004/028536 | 4/2004 |
| WO | WO 2005/084635 | 9/2005 |
| WO | WO 2006/047080 | 5/2006 |
| WO | WO 2007/011874 | 1/2007 |
| WO | WO 2008/120070 | 10/2008 |
| WO | WO 2010/054135 | 5/2010 |
| WO | WO 2010/147962 | 12/2010 |

OTHER PUBLICATIONS

Atmaca, Gulizar, Antioxidant Effects of Sulfur-Containing Amino Acids, Yonsei Medical Journal, 2004, 45 (5), 776-788.*

(Continued)

*Primary Examiner* — Ali Soroush
*Assistant Examiner* — Genevieve S Alley
(74) *Attorney, Agent, or Firm* — Sterne, Kessler, Goldstein & Fox PLLC

(57) ABSTRACT

Compounds, formulations, and methods are provided containing the choline ester of a reducing agent, especially lipoic acid or derivatives thereof. The compounds may be administered via a topical ocular route to treat or prevent oxidative damage.

12 Claims, 5 Drawing Sheets

(56) References Cited

U.S. PATENT DOCUMENTS

| | | |
|---|---|---|
| 7,914,815 B2 | 3/2011 | Till et al. |
| 7,935,332 B2 | 5/2011 | Till |
| 8,147,816 B2 | 4/2012 | Till et al. |
| 8,410,162 B2 | 4/2013 | Garner et al. |
| 8,647,612 B2 | 2/2014 | Garner et al. |
| 8,697,109 B2 | 4/2014 | Garner et al. |
| 8,747,829 B2 | 6/2014 | Till et al. |
| 8,795,706 B2 | 8/2014 | Garner et al. |
| 9,044,439 B2 | 6/2015 | Garner at al. |
| 2002/0025311 A1 | 2/2002 | Till |
| 2002/0035243 A1 | 3/2002 | Imfeld et al. |
| 2003/0187058 A1 | 10/2003 | Hasselwander et al. |
| 2003/0228299 A1 | 12/2003 | Droy-Lefaix et al. |
| 2004/0044227 A1 | 3/2004 | Klatt et al. |
| 2004/0092586 A1 | 5/2004 | Ogata at al. |
| 2005/0101677 A1 | 5/2005 | Till |
| 2005/0112113 A1 | 5/2005 | Till et al. |
| 2005/0130881 A1 | 6/2005 | Shashoura et al. |
| 2005/0137124 A1 | 6/2005 | Castillejos |
| 2005/0171212 A1 | 8/2005 | Gierhart et al. |
| 2005/0287201 A1 | 12/2005 | Till at al. |
| 2006/0177430 A1 | 8/2006 | Bhushan |
| 2006/0188492 A1 | 8/2006 | Richardson et al. |
| 2007/0055070 A1 | 3/2007 | Lawrence |
| 2007/0099845 A1 | 5/2007 | Sheu et al. |
| 2007/0207116 A1 | 9/2007 | Brown |
| 2007/0293562 A1 | 12/2007 | Mylari et al. |
| 2008/0038316 A1 | 2/2008 | Wong et al. |
| 2008/0139990 A1 | 6/2008 | Till et al. |
| 2008/0213239 A1 | 9/2008 | Morris |
| 2009/0082281 A1 | 3/2009 | Shashoua |
| 2009/0093541 A1 | 4/2009 | Ogata |
| 2009/0192212 A1 | 7/2009 | Garner et al. |
| 2010/0098653 A1 | 4/2010 | Yu et al. |
| 2011/0135622 A1 | 6/2011 | Till et al. |
| 2014/0121266 A1 | 5/2014 | Garner et al. |
| 2014/0243385 A1 | 8/2014 | Garner et al. |
| 2014/0336562 A1 | 11/2014 | Till et al. |
| 2014/0357691 A1 | 12/2014 | Garner et al. |

OTHER PUBLICATIONS

Al-Ghoul, K. J., R. K. Nordgren, A. J. Kuszak, C. D. Freel, M. J. Costello, and J. R. Kuszak. 2001. Structural evidence of human nuclear fiber compaction as a function of ageing and cataractogenesis. Experimental eye research 72: 199-214.

Applegate, M. A., K. M. Humphries, and L. I. Szweda. Jan. 2007. Reversible Inhibition of alpha-Ketoglutarate Dehydrogenase by Hydrogen Peroxide: Glutathionylation and Protection of Lipoic Acid. Biochemistry. 47(1): 473-478.

Argirova, M., M. Kleine-Reidick, and W. Breipohl. 2004. Redox status of the eye lens: a regional study. Cell biochemistry and biophysics 41: 381-390.

Ariga T, et al. 2000. Antithrombotic and antineoplastic effects of phyto-organosulfur compounds. Biofactors. 13(1-4):251-5.

Arora A, et al. 2004. Reversal of P-glycoprotein-mediated multidrug resistance by diallyl sulfide in K562 leukemic cells and in mouse liver. Carcinogenesis. 25(6):941-9. Epub Jan. 16, 2004.

Asmellash S, et al. 2005. Modulating the endoplasmic reticulum stress response with trans-4,5-dihydroxy-1,2-dithiane prevents chemically induced renal injury in vivo. Toxicol Sci. 88(2):576-84. Epub Sep. 8, 2005.

Baghieri, S., and M. H. Garner. 1992. Na,K-ATPase and phospholipid degradation in bovine and human lenses. Current eye research 11: 459-467.

Belloir C, et al. 2006. Protective effects of garlic sulfur compounds against DNA damage induced by direct- and indirect-acting genotoxic agents in HepG2 cells. Food Chem Toxicol. 44(6):827-34.

Bilska, A., and L. Wlodek. 2005. Lipoic acid—the drug of the future? Pharmacol Rep 57: 570-577.

Bilska, A., M. Dubiel, M. Sokolowska-Jezewicz, E. Lorenc-Koci, and L. Wlodek. Jun. 2007. Alpha-lipoic acid differently affects the reserpine-induced oxidative stress in the striatum and prefrontal cortex of rat brain. Neuroscience 146: 1758-1771.

Bitar, M. S., S. Wahid, C. W. Pilcher, E. Al-Saleh, and F. Al-Mulla. 2004. Alpha-lipoic acid mitigates insulin resistance in Goto-Kakizaki rats. Hormone and metabolic research. Hormon- und Stoffwechselforschung 36: 542-549.

Blanco, R. A., T. R. Ziegler, B. A. Carlson, P. Y. Cheng, Y. Park, G. A. Cotsonis, C. J. Accardi, and D. P. Jones. Oct. 2007. Diurnal variation in glutathione and cysteine redox states in human plasma. The American journal of clinical nutrition 86: 1016-1023.

Blankenship, T. N., J. F. Hess, and P. G. FitzGerald. 2001. Development- and differentiation-dependent reorganization of intermediate filaments in fiber cells. Investigative ophthalmology & visual science 42: 735-742.

Bonomi, L et al. 1990. Evaluation of the 701 interzeag lens opacity meter. Graefe's Arch Clin Exp Ophthalmol 228(5):447-9.

Borja. D et al. Jun. 2008. Optical Power of the Isolated Human Crystalline Lens. Invest Ophthalmol Vis Sci 49(6):2541-8.

Bron, A.J., et al. "The Ageing Lens" Ophthalmologica (2000) 214(1):86-104.

Brunkener, M., and S. D. Georgatos. 1992. Membrane-binding properties of filensin, a cytoskeletal protein of the lens fiber cells. Journal of cell science 103 ( Pt 3): 709-718.

Cenedella, R. J. 1998. Prenylation of proteins by the intact lens. Investigative ophthalmology & visual science 39: 1276-1280.

Croft, M. A., A. Glasser, G. Heatley, J. McDonald, T. Ebbert, N. V. Nadkarni, and P. L. Kaufman. 2006. The zonula, lens, and circumlental space in the normal iridectomized rhesus monkey eye. Investigative ophthalmology & visual science 47: 1087-1095.

Croft, M. A., and P. L. Kaufman. 2006. Accommodation and presbyopia: the ciliary neuromuscular view. Ophthalmology clinics of North America 19: 13-24, v.

Dubbelman, M., G. L. Van der Heijde, H. A. Weeber, and G. F. Vrensen. 2003. Changes in the internal structure of the human crystalline lens with age and accommodation. Vision research 43: 2363-2375.

Eason, R. C., H. E. Archer, S. Akhtar, and C. J. Bailey. 2002. Lipoic acid increases glucose uptake by skeletal muscles of obese-diabetic ob/ob mice. Diabetes Obes Metab 4: 29-35.

Egan, D., P. James, D. Cooke, and R. O'Kennedy. 1997. Studies on the cytostatic and cytotoxic effects and mode of action of 8-nitro-7-hydroxycoumarin. Cancer letters 118: 201-211.

Finn, G., B. Creaven, and D. Egan. 2003. Modulation of mitogen-activated protein kinases by 6-nitro-7-hydroxycoumarin mediates apoptosis in renal carcinoma cells. European journal of pharmacology 481: 159-167.

Finn, G. J., B. S. Creaven, and D. A. Egan. 2004. A study of the role of cell cycle events mediating the action of coumarin derivatives in human malignant melanoma cells. Cancer letters 214: 43-54.

Flammer J, Bebie H. 1987. Lens Opacity Meter: a new instrument to quantify lens opacity. Ophthalmologica 195(2):69-72.

Furuta, T., S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. Proceedings of the National Academy of Sciences of the United States of America 96: 1193-1200.

Gail MH & You WC. 2006. A factorial trial including garlic supplements assesses effect in reducing precancerous gastric lesions. J Nutr. 136(3 Suppl):813S-815S.

Garner, M. H., and J. Horwitz. 1994. Catalytic subunit isoforms of mammalian lens Na,K-ATPase. Current eye research 13: 65-77.

Garner, M. H., and Y. Kong. 1999. Lens epithelium and fiber Na,K-ATPases: distribution and localization by immunocytochemistry. Investigative ophthalmology & visual science 40: 2291-2298.

(56) References Cited

OTHER PUBLICATIONS

Garner, M. H., and J. R. Kuszak. 1993. Cations, oxidants, light as causative agents in senile cataracts. Puerto Rico health sciences journal 12: 115-122.
Garner, M. H., and A. Spector. 1980. Selective oxidation of cysteine and methionine in normal and senile cataractous lenses. Proceedings of the National Academy of Sciences of the United States of America 77: 1274-1277.
Garner, M. H. 1994. Na,K-ATPases of the lens epithelium and fiber cell: formation of catalytic cycle intermediates and Na+: K+ exchange. Experimental eye research 58: 705-718.
Gilmore WJ & Kirby GM. 2004. Endoplasmic reticulum stress due to altered cellular redox status positively regulates murine hepatic CYP2A5 expression. J Pharmacol Exp Ther. 308(2):600-8. Epub Nov. 10, 2003.
Glasser, A., and M. C. Campbell. 1999. Biometric, optical and physical changes in the isolated human crystalline lens with age in relation to presbyopia. Vision research 39: 1991-2015.
Goulielmos, G., F. Gounari, S. Remington, S. Muller, M. Haner, U. Aebi, and S. D. Georgatos. 1996. Filensin and phakinin form a novel type of beaded intermediate filaments and coassemble de novo in cultured cells. The Journal of cell biology 132: 643-655.
Goulielmos, G., S. Remington, F. Schwesinger, S. D. Georgatos, and F. Gounari. 1996. Contributions of the structural domains of filensin in polymer formation and filament distribution. Journal of cell science 109 ( Pt 2): 447-456.
Green DR & Reed JC. 1998. Mitochondria and apoptosis. Science 281(5381):1309-12.
Gruzman, A., A. Hidmi, J. Katzhendler, A. Haj-Yehie, and S. Sasson. 2004, Synthesis and characterization of new and potent alpha-lipoic acid derivatives. Bioorganic & medicinal chemistry 12: 1183-1190.
Guest, P. C., H. A. Skynner, K. Salim, F. D. Tattersall, M. R. Knowles, and J. R. Atack. 2006. Detection of gender differences in rat lens proteins using 2-D-DIGE. Proteomics 6: 667-676.
Gurney, AM. 1994. Flash photolysis of caged compounds in Microelectrode Techniques, ed Ogden D, pp. 389-406.
Halhal M, et al. 2004. Iontophoresis: from the lab to the bed side. Exp Eye Res 78(3):751-57.
Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.
Hardie, R.C. 1995. Photolysis of Caged Ca2+ Facilitates and inactivates but Does Not Directly Excite Light-Sensitive Channels in *Drosophila* Photoreceptors, The Journal of Neuroscience 15(1):899-902.
Heidemann, S. R., S. Kaech, R. E. Buxbaum, and A. Matus. 1999. Direct observations of the mechanical behaviors of the cytoskeleton in living fibroblasts. The Journal of cell biology 145: 109-122.
Hermans, E., M. Dubbelman, R. van der Heijde, and R. Heethaar. Jul. 2007. The shape of the human lens nucleus with accommodation. Journal of vision 7: 16.1-10.
Hoenders, H.J., et al. "Lens proteins and aging" J Gerontol (May 1983) 38(3):278-86.
Hofmann, M., P. Mainka, H. Tritschler, J. Fuchs, and G. Zimmer. 1995. Decrease of red cell membrane fluidity and -SH groups due to hyperglycemic conditions is counteracted by alpha-lipoic acid. Archives of biochemistry and biophysics 324: 85-92.
Hung CC, et al. 2003. Protection of renal epithelial cells against oxidative injury by endoplasmic reticulum stress preconditioning is mediated by ERK1/2 activation. J Biol Chem. 278(31):29317-26. Epub May 8, 2003.
Ivanov, D., G. Dvoriantchikova, A. Pestova, L. Nathanson, and V. I. Shestopalov. 2005. Microarray analysis of fiber cell maturation in the lens. FEBS letters 579: 1213-1219.
Janoria, K. G., S. Hariharan, D. Paturi, D. Pal, and A. K. Mitra. 2006. Biotin uptake by rabbit corneal epithelial cells: role of sodium-dependent multivitamin transporter (SMVT). Current eye research 31: 797-809.

Jimenez-Orozco, F. A., J. S. Lopez-Gonzalez, A. Nieto-Rodriguez, M. A. Velasco-Velazquez, J. A. Molina-Guarneros, N. Mendoza-Patino, M. J. Garcia-Mondragon, P. Elizalde-Galvan, F. Leon-Cedeno, and J. J. Mandoki. 2001. Decrease of cyclin D1 in the human lung adenocarcinoma cell line A-427 by 7-hydroxycoumarin. Lung cancer (Amsterdam, Netherlands) 34: 185-194.
Johansson, M., and M. Lundberg. Dec. 2007. Glutathionylation of beta-actin via a cysteinyl sulfenic acid intermediary. BMC Biochem 8: 26.
Jones, D. P., Y. M. Go, C. L. Anderson, T. R. Ziegler, J. M. Kinkade, Jr., and W. G. Kirlin. 2004, Cysteine/cystine couple is a newly recognized node in the circuitry for biologic redox signaling and control. Faseb J 18: 1246-1248.
Jung MY, et al. 2001. Chemopreventive allylthiopyridazine derivatives induce apoptosis in SK-Hep-1 hepatocarcinoma cells through a caspase-3-dependent mechanism. Eur J Cancer. 37(16):2104-10.
Jürgen, W. Mar. 2007. Synthesis and investigations of (6-hydroxy-3-oxo-3H-xanthen-9-yl)methyl derivatives. A new photoremovable protecting group. Inaugural Dissertation at Universität Basel.
Kahn, J., P. Preis, F. Waldman, and A. Tseng, Jr. 1994. Coumarin modulates the cell-cycle progression of an MTV-EJras cell line. Journal of cancer research and clinical oncology 120 Suppl: S19-22.
Kao, J.P.Y. 2006. Caged Molecules: Principles and Practical Considerations. Current Protocols in Neuroscience. 6.20.1-6.20.21.
Kibbelaar, M. A., F. C. Ramaekers, P. J. Ringens, A. M. Selten-Versteegen, L. G. Poels, P. H. Jap, A. L. van Rossum, T. E. Feltkamp, and H. Bloemendal. 1980. Is actin in eye lens a possible factor in visual accomodation? Nature 285: 506-508.
Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.
Konrad, D., R. Somwar, G. Sweeney, K. Yaworsky, M. Hayashi, T. Ramlal, and A. Klip. 2001. The antihyperglycemic drug alpha-lipoic acid stimulates glucose uptake via both GLUT4 translocation and GLUT4 activation: potential role of p38 mitogen-activated protein kinase in GLUT4 activation. Diabetes 50: 1464-1471.
Krueger, R.R., et al. "Experimental increase in accommodative potential after neodymium: yttrium-aluminum-garnet laser photodisruption of paired cadaver lenses" Ophthalmology (2001) 108(11):2122-29. (Abstract only).
Krumdieck, C.L., et al. "Mechanism of Homocysteine Toxicity on Connective Tissues: Implications for the Morbidity of Aging" J. Nutr. (2000) 130:365S-68S.
Kumar RV, et al. 1991. The nature of inhibition of 3-hydroxy-3-methylglutaryl CoA reductase by garlic-derived diallyl disulfide. Biochim Biophys Acta. 1078(2):219-25.
Kuszak, J. R., A. R. Khan, and R. J. Cenedella. 1988. An ultrastructural analysis of plasma membrane in the U18666A cataract. Investigative ophthalmology & visual science 29: 261-267.
Lacy, A., and R. O'Kennedy. 2004. Studies on coumarins and coumarin-related compounds to determine their therapeutic role in the treatment of cancer. Current pharmaceutical design 10: 3797-3811.
Larsson, H. P., A. V. Tzingounis, H. P. Koch, and M. P. Kavanaugh. 2004. Fluorometric measurements of conformational changes in glutamate transporters. Proceedings of the National Academy of Sciences of the United States of America 101: 3951-3956.
Lee V & Bundgaard H. 1992. Improved Ocular Drug Delivery with Prodrugs. In: Sloan K. ed. Produgs: Topical and Ocular Drug Delivery, vol. 53, p. 233.
Lesiński L. & Duschmalé J. 2006. Flash Photolysis in Praktikum "Physikalische Chemie" pp. 1-8.
Li, L., J. Lim, M. D. Jacobs, J. Kistler, and P. J. Donaldson. Mar. 2007. Regional differences in cystine accumulation point to a sutural delivery pathway to the lens core. Investigative ophthalmology & visual science 48: 1253-1260.
Lim, J., Y. C. Lam, J. Kistler, and P. J. Donaldson. 2005. Molecular characterization of the cystine/glutamate exchanger and the excitatory amino acid transporters in the rat lens. Investigative ophthalmology & visual science 46: 2869-2877.

(56) References Cited

OTHER PUBLICATIONS

Lim, J., L. Li, M. D. Jacobs, J. Kistler, and P. J. Donaldson. Nov. 2007. Mapping of glutathione and its precursor amino acids reveals a role for GLYT2 in glycine uptake in the lens core. Investigative ophthalmology & visual science 48: 5142-5151.
Lindsey Rose, K. M., R. G. Gourdie, A. R. Prescott, R. A. Quinlan, R. K. Crouch, and K. L. Schey. 2006. The C terminus of lens aquaporin 0 interacts with the cytoskeletal proteins filensin and CP49. Investigative ophthalmology & visual science 47: 1562-1570.
Liu H, et al. 1997. Endoplasmic reticulum chaperones GRP78 and calreticulin prevent oxidative stress. Ca2+ disturbances, and cell death in renal epithelial cells. J Biol Chem. 272(35):21751-9.
Liu, J., E. Head, A. M. Gharib, W. Yuan, R. T. Ingersoll, T. M. Hagen, C. W. Cotman, and B. N. Ames. 2002. Memory loss in old rats is associated with brain mitochondrial decay and RNA/DNA oxidation: partial reversal by feeding acetyl-L-carnitine and/or R-alpha-lipoic acid. Proceedings of the National Academy of Sciences of the United States of America 99: 2356-2361.
Lopez-Gonzalez, J. S., H. Prado-Garcia, D. Aguilar-Cazares, J. A. Molina-Guarneros, J. Morales-Fuentes, and J. J. Mandoki, 2004. Apoptosis and cell cycle disturbances induced by coumarin and 7-hydroxycoumarin on human lung carcinoma cell lines. Lung cancer (Amsterdam, Netherlands) 43: 275-283.
Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. Mol Pharm 3: 329-339.
Maitra, I., E. Serbinova, H. J. Tritschler, and L. Packer. 1996. Stereospecific effects of R-lipoic acid on buthionine sulfoximine-induced cataract formation in newborn rats. Biochemical and biophysical research communications 221: 422-429.
Maitra, I., E. Serbinova, H. Trischler, and L. Packer. 1995. Alpha-lipoic acid prevents buthionine sulfoximine-induced cataract formation in newborn rats. Free radical biology & medicine 18: 823-829.
Manns, F., J. M. Parel, D. Denham, C. Billotte, N. Ziebarth, D. Borja, V. Fernandez, M. Aly, E. Arrieta, A. Ho, and B. Holden. Jul. 2007. Optomechanical response of human and monkey lenses in a lens stretcher. Investigative ophthalmology & visual science 48: 3260-3268.
Merdes, A., M. Brunkener, H. Horstmann, and S. D. Georgatos. 1991. Filensin: a new vimentin-binding, polymerization-competent, and membrane-associated protein of the lens fiber cell. The Journal of cell biology 115: 397-410.
Merdes, A., F. Gounari, and S. D. Georgatos. 1993. The 47-kD lens-specific protein phakinin is a tailless intermediate filament protein and an assembly partner of filensin. The Journal of cell biology 123: 1507-1516.
Moffat, B.A., et al. "Age-related Changes in the Kinetics, of Water Transport in Normal Human Lenses" Exp. Eye Res. (1999) 69(6):663-69.
Moini, H., O. Tirosh, Y. C. Park, K. J. Cho, and L. Packer. 2002. R-alpha-lipoic acid action on cell redox status, the insulin receptor, and glucose uptake in 3T3-L1 adipocytes. Archives of biochemistry and biophysics 397: 384-391.
Muchowski, P. J., M. M. Valdez, and J. I. Clark. 1999. AlphaB-crystallin selectively targets intermediate filament proteins during thermal stress. Investigative ophthalmology & visual science 40: 951-958.
Musk SR, et al. 1997. Cytotoxicity and genotoxicity of diallyl sulfide and diallyl disulfide towards Chinese hamster ovary cells. Food Chem Toxicol. 35(3-4):379-85.
Newell. 1996. Ophthalmology: Principles and Concepts St. Louis: Mosby-Year Book St. Louis, p. 83.
Obrosova I, et al. 1998. Diabetes-induced changes in lens antioxidant status, glucose utilization and energy metabolism: effect of DL-alpha-lipoic acid. Diabetologia 41(12):1442-50.
Ong, M. D., D. M. Payne, and M. H. Garner. 2003. Differential protein expression in lens epithelial whole-mounts and lens epithelial cell cultures. Experimental eye research 77: 35-49.
Pau, H., and J. Kranz. 1991. The increasing sclerosis of the human lens with age and its relevance to accommodation and presbyopia. Graefe's archive for clinical and experimental ophthalmology = Albrecht von Graefes Archiv fur klinische und experimentelle Ophthalmologie 229: 294-296.
Petit PX, et al. 1995. Alterations in mitochondrial structure and function are early events of dexamethasone-induced thymocyte apoptosis. J Cell Biol. 130(1 ):157-67.
Phelps-Brown, N.A., et al. "Nutritional supplements and the eye" Eye (1998) 12:127-33.
Pierscionek, B. K. 1995. Age-related response of human lenses to stretching forces. Experimental eye research 60: 325-332.
Reddy, N. S., K. Gumireddy, M. R. Mallireddigari, S. C. Cosenza, P. Venkatapuram, S. C. Bell, E. P. Reddy, and M. V. Reddy. 2005. Novel coumarin-3-(N-aryl)carboxamides arrest breast cancer cell growth by inhibiting ErbB-2 and ERK1. Bioorganic & medicinal chemistry 13: 3141-3147.
Salvioli S, et al. 1997. JC-1, but not DiOC6(3) or rhodamine 123, is a reliable fluorescent probe to assess delta psi changes in intact cells: implications for studies on mitochondrial functionality during apoptosis. FEBS Lett. 411(1):77-82.
Sandilands, A., A. R. Prescott, A. M. Hutcheson, R. A. Quinlan, J. T. Casselman, and P. G. FitzGerald. 1995. Filensin is proteolytically processed during lens fiber cell differentiation by multiple independent pathways. European journal of cell biology 67: 238-253.
Sarraf D & Lee DA. 1994. The Role of Iontophoresis in Ocular Drug Delivery. J Ocul Pharmacol 10(1):69-81.
Sato, H., M. Tamba, K. Kuriyama-Matsumura, S. Okuno, and S. Bannai. 2000. Molecular cloning and expression of human xCT, the light chain of amino acid transport system xc. Antioxid Redox Signal 2: 665-671.
Sato, H., M. Tamba, T. Ishii, and S. Bannai. 1999. Cloning and expression of a plasma membrane cystine/glutamate exchange transporter composed of two distinct proteins. The Journal of biological chemistry 274: 11455-11458.
Sato, H., A. Shiiya, M. Kimata, K. Maebara, M. Tamba, Y. Sakakura, N. Makino, F. Sugiyama, K. Yagami, T. Moriguchi, S. Takahashi, and S. Bannai. 2005. Redox imbalance in cystine/glutamate transporter-deficient mice. The Journal of biological chemistry 280: 37423-37429.
Schonheit, K., L. Gille, and H. Nohl. 1995. Effect of alpha-lipoic acid and dihydrolipoic acid on ischemia/reperfusion injury of the heart and heart mitochondria. Biochimica et biophysica acta 1271: 335-342.
Senda, N. 2006. Synthesis and Photochemical Properties of a New Water-Soluble Coumarin, Designed as a Chromophore for Highly Water-Soluble and Photolabile Protecting Group. Bull. Chem. Soc. Jpn. vol. 79, No. 11, 1753-1757.
Shembekar, V. R., Y. Chen, B. K. Carpenter, and G. P. Hess. 2005. A protecting group for carboxylic acids that can be photolyzed by visible light. Biochemistry 44: 7107-7114.
Spector, A., et al. "Thioredoxin fragment 31-36 is reduced by dihydrolipoamide and reduces oxidized protein" Biochem Biophys Res Commun (Jan. 1988) 150(1):156-62.
Strenk, S. A., L. M. Strenk, J. L. Semmlow, and J. K. DeMarco. 2004. Magnetic resonance imaging study of the effects of age and accommodation on the human lens cross-sectional area. Investigative ophthalmology & visual science 45: 539-545.
Sundaram SG & Milner JA. 1996. Diallyl disulfide suppresses the growth of human colon tumor cell xenografts in athymic nude mice. J Nutr. 126(5):1355-61.
Sweeney, M. H., and R. J. Truscott. 1998. An impediment to glutathione diffusion in older normal human lenses: a possible precondition for nuclear cataract. Experimental eye research 67: 587-595.
Tamm, E., E. Lutjen-Drecoll, W. Jungkunz, and J. W. Rohen. 1991. Posterior attachment of ciliary muscle in young, accommodating old, presbyopic monkeys. Investigative ophthalmology & visual science 32: 1678-1692.
Tamm, S., E. Tamm, and J. W. Rohen. 1992. Age-related changes of the human ciliary muscle. A quantitative morphometric study. Mechanisms of ageing and development 62: 209-221.

(56) References Cited

OTHER PUBLICATIONS

Truscott, R. J. 2000. Age-related nuclear cataract: a lens transport problem. Ophthalmic research 32: 185-194.
Wang, C. J., Y. J. Hsieh, C. Y. Chu, Y. L. Lin, and T. H. Tseng. 2002. Inhibition of cell cycle progression in human leukemia HL-60 cells by esculetin. Cancer letters 183; 163-168.
Wang, S. J., and H. H. Chen. Jan. 2007. Presynaptic mechanisms underlying the alpha-lipoic acid facilitation of glutamate exocytosis in rat cerebral cortex nerve terminals. Neurochemistry international 50: 51-60.
Weeber, HA et al. Feb. 2007. Stiffness gradient in the crystalline lens. Graefes Arch Clin Exp Ophthalmol 245(9):1357-66.
Widomska, J., M. Raguz, J. Dillon, E. R. Gaillard, and W. K. Subczynski. Jun. 2007. Physical properties of the lipid bilayer membrane made of calf lens lipids: EPR spin labeling studies. Biochimica et biophysics acta 1768: 1454-1465.
Wieboldt, R. et al. 1994. Photolabile precursors of glutamate: Synthesis, photochemical properties, and activation of glutamate receptors on a microsecond time scale. Proc. Natl. Acad. Sci, 91:8752-8756.
Willner I & Zahavy E. 1994. Activation of Glutathione Reducase by Light: A Novel Approach to Design Redox Photo-Enzymes. Angew Chem Int Ed Engl 33(5):581-83.
Yin MC, et al. 2002. Nonenzymatic antioxidant activity of four organosulfur compounds derived from garlic. J Agric Food Chem. 50(21):6143-7.
Yu, N. T., D. C. DeNagel, P, L. Pruett, and J. F. Kuck, Jr. 1985. Disulfide bond formation in the eye lens. Proceedings of the National Academy of Sciences of the United States of America 82: 7965-7968.
Zhao, Y., Q. Zheng, K. Dakin, K. Xu, M. L. Martinez, and W. H. Li. 2004. New caged coumarin fluorophores with extraordinary uncaging cross sections suitable for biological imaging applications. Journal of the American Chemical Society 126: 4653-4663.
Zivkovic D. Apr. 2007. Investigations on 2,7-diamino-9-fluorenol photochemistry. Inaugural Dissertation at Universität Basel.
Ip C, Ganther HE. 1992. Comparison of selenium and sulfur analogs in cancer prevention. Carcinogenesis. 13(7): 1167-70.
Bustamante, J., et al., 1998. α-Lipoic Acid in Liver Metabolism and Disease. Free Radical Biology & Medicine 24: No. 6 1023-1039.
Cagini, C. MD, et al. 2010. Study of alpha-lipoic acid penetration in the human aqueous humour after topical administration. Clinical and Experimental Ophthalmology "Accepted Article" doi: 10.1111/j.1442-9071.2010.02319.x.
Giblin FJ, et al. 1979. The effects of X-irradiation on lens reducing systems. Investigative Ophthalmology & Visual Science 18:468-475.
Kramár P, et al. 1987. Thermal cataract formation in rabbits. NCBI Pubmed abstract, PMID: 3426637, abstract of Bioelectromagnetics 8:397-406. (Abstract only).
Li, X., Liu, Z., et al. Apr. 2008. Lipoamide protects retinal pigment epithelial cells from oxidative stress and mitochondrial dysfunction. Free Radic Biol Med. 44(7): 1465-1474.
Lipman RM, et al. 1988. Cataracts induced by Microwave and Ionizing Radiation. NCBI Pubmed abstract, PMID: 3068822, abstract of Surv. Ophthalmol 33:200-210. (Abstract only).

Trayhurn P. and Van Heyningen R. 1973. The Metabolism of Amino Acids in the Bovine Lens; Their Oxidation as a Source of Energy. Biochem. J. 136:67-75.
Wakabayashi, Y. et al. 2006. Glutamate Levels in Aqueous Humor of Patients with Retinal Artery Occlusion. Retina 26:432-436.
Zwingmann, C. et al. 2001. 13C Isotopomer Analysis of Glucose and Alanine Metabolism Reveals Cytosolic Pyruvate Compartmentation as Part of Energy Metabolism in Astrocytes. GLIA 34:200-212.
Aloisi et al. 1948. Glycerylphosphorylcholine and Choline Glycerophosphate. Biochemical Journal. vol. 43, pp. 157-161; p. 157, col. 1, para 2-3; col. 2, par 1; p. 158, col. 1, para 4.
Gilbert, Basic Concepts in Biochemistry USA. McGraw Hill 2000 p. 184.
Jablonski et al. Plant Physiology 1978 61:221-225.
Ng et al. Experimental Eye Research 1986 43:477-489.
Morris Jr. Recent advances in arginine metabolism; roles and regulation of the arginases. British Journal of Pharmacology, E-Pub Jun. 5, 2009, 157(6):922-930.
PubChem Compound Summary CID 863 lipoamide (Sep. 16, 2004) (Retrieved from the internet Nov. 13, 2010; http://pubchem.ncbi.nlm.nih.gov/summary/summary.cgi?cid=863.
Salceda, et al. L-arginine uptake in normal and diabetic rat retina and retinal pigment epithelium. Neurochem Res., Aug. 2008, 33(8):1541-1545.
Stuehr et al. Nw-Hydroxy-L-arginine is an intermediate in the Biosynthesis of nitric Oxide from L-Arginine. The Journal of Biological Chemistry 1991, 266(10);6259-6263.
Truscott. Presbyopia. Emerging from a blur towards an understanding of the molecular basis for this most common eye condition. Exp Eye Res., Epub Jul. 2008, 88(2):241-247; p. 241, col. 1; p. 242, col. 1; p. 245, col. 1.
English Translation of Office Action mailed Jun. 21, 2011, in Japanese Patent Application No. JP 2007-537922 A, filed Dec. 27, 2007.
Extended European Search Report mailed on Apr. 19, 2012, for EP Application No. 09825411.0, European Patent Office, Germany.
Office Action received in U.S. Appl. No. 12/815,586 dated May 9, 2012.
Extended European Search Report mailed on Aug. 21, 2012, for EP Application No. 10790038.3, European Patent Office, Netherlands.
English Translation of Office Action mailed Oct. 12, 2012, in Mexican Patent Application No. MX/a/2007/004775.
Glasser, A., "Restoration of accommodation: surgical options for correction of presbyopia," *Clin Exp Optom* 91(3):279-295, Australian Optometrists Association, Australia (May 2008).
McGinty, S. J., and Truscott, R. J. W., "Presbyopia: the first stage of nuclear cataract?" *Opthalmic Res* 38(3):137-148, Karger, Switzerland (Jan. 2006).
Michael, R., and Bron, A. J., "The ageing lens and cataract: a model of normal and pathological ageing," *Phil. Trans. R. Soc. B* 366(1568):1278-1292. The Royal Society, England (Mar. 2011).
Truscott, R J. W., and Zhu, X., "Presbyopia and cataract: a question of heat and time," *Prog Retia Eye Res* 29(6):487-499, Elesevier Ltd., England (Nov. 2010).
Co-pending U.S. Appl. No. 14/697,205, inventors Garner et al., filed Apr. 27, 2015, (Not Published).

\* cited by examiner

CHOLINE ESTERS

CROSS-REFERENCE TO RELATED APPLICATIONS

This application claims the benefit of U.S. Provisional Application Nos. 61/187,005 filed Jun. 15, 2009, 61/224,930 filed Jul. 13, 2009, and 61/242,232 filed Sep.14, 2009, each of which is incorporated by reference in its entirety.

BACKGROUND OF THE INVENTION

As we age, our lenses undergo physiological changes that make it more difficult to focus on near objects. That is why nearly everyone requires reading glasses, even as early as age 35-40. The ability of the eye to change focal power, also known as accommodative amplitude, decreases significantly with age. The accommodative amplitude is 20 diopters in children and young adults, but it decreases to 10 diopters by age 25 and to ≤1 diopter by age 60. The age-related inability to focus on near objects is called presbyopia. All of us will develop presbyopia and will use corrective lenses unless a new treatment is found.

Both presbyopia and cataract are age-related and may share common etiologies such as lens growth, oxidative stress, and/or disulfide bond formation.

There is a need for compositions, formulations and methods for combating presbyopia and/or cataract, particularly compositions and methods that minimize toxicity to surrounding healthy tissues.

BRIEF SUMMARY OF THE INVENTION

In one embodiment, a compound is provided that is the choline ester of lipoic acid or a derivative of lipoic acid. In one embodiment, the lipoic acid is alpha lipoic acid. In another embodiment, the derivative of lipoic acid is: 6,8-dimercaptooctanoic acid; dihydrolipoate; 5-(1,2-thiaselenolan-5-yl)pentanoic acid; or 5-(1,2-thiaselenolan-3-yl)pentanoic acid. The lipoic acid or derivative of lipoic acid can include the R enantiomer.

In another embodiment, a pharmaceutical composition is provided comprising an active agent that is a reducing agent-choline ester at least one pharmaceutically acceptable excipient. In one embodiment, the reducing agent is lipoic acid or a derivative thereof, e.g., lipoic acid choline ester. The active agent can be present in an amount of about 0.1% to about 10%, more specifically about 0.5% to about 10%.

In one embodiment, the pharmaceutical composition includes a buffer, a tonicity agent, and/or a viscosity agent. In one embodiment, the buffet is a phosphate buffer. In another embodiment, the viscosity agent is a cellulosic agent.

In one embodiment, the pharmaceutical composition includes a biochemical energy source, e.g. pyruvate or alanine.

In one embodiment, the pharmaceutical composition has a pH of about 4 to about 7.5. In another embodiment, the pharmaceutical composition has a pH of about 5 to about 6.

In one embodiment, the pharmaceutical composition is suitable for topical ocular delivery, e.g., an eye drop.

In one embodiment, a pharmaceutical composition is provided that contains:
about 0.25% to about 10% of a reducing agent-choline ester,
optionally, about 0.05% to about 1.0% of a biochemical energy source,
about 0.25% to about 1% buffer,
about 0.2% to about 0.6% tonicity agent, and
about 0.1% to about 0.4% viscosity agent.

In another embodiment, a pharmaceutical composition is provided that contains:
5% lipoic acid choline ester,
0.1% ethyl pyruvate,
0.269% sodium phosphate monobasic monohydrate,
0.433% sodium phosphate dibasic anhydrous,
0.5% sodium chloride, and
0.2% hydroxypropyl methylcellulose.

In another embodiment, a pharmaceutical composition is provided that contains:
5.0% lipoic acid choline ester,
0.5% alanine,
0.269% sodium phosphate monobasic monohydrate,
0.433% sodium phosphate dibasic anhydrous,
0.5% sodium chloride, and
0.2 hydroxypropyl methylcellulose.

In yet another embodiment, a method of preventing or treating oxidation damage to cells is provided by administering the pharmaceutical composition. The method can optionally include administering a biochemical energy source.

In one embodiment, the cells are in vivo. In another embodiment, the cells are ocular cells.

In one embodiment, administering is administering by topical ocular delivery.

In another embodiment, a method is provided for a one-step synthesis comprising reacting a reducing agent (e.g., lipoic acid) with a halogenated choline (e.g., bromocholine bromide) to yield a choline ester.

In another embodiment, a small portion of the DHLA-thiolactone can react with low pK lysine protein residues to form a post-translational acylation product, denoted as Nepsilon-lipoyl group.

DETAILED DESCRIPTION OF THE INVENTION

Figure 1:
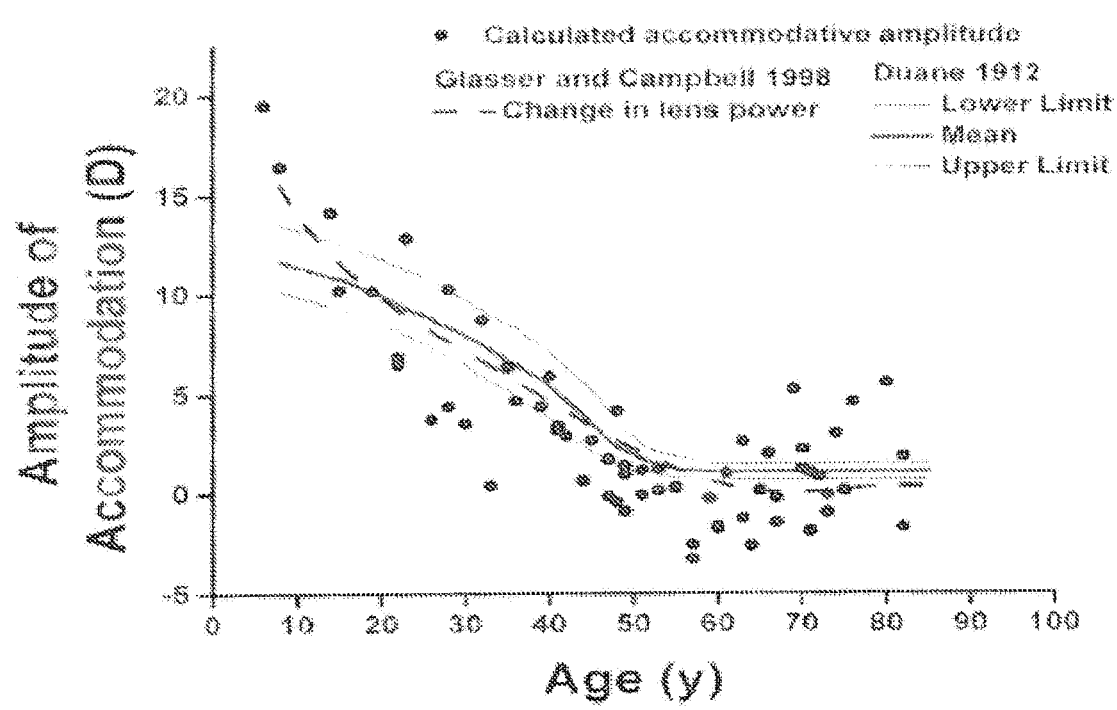
FIG. 1 depicts the accommodative amplitude in diopters (D) of an untreated human lens as a function of age in years. Borja, D et al. 2008. Optical Power of the Isolated Human Crystalline Lens, Invest Ophthalmol Vis Sci 49(6):2541-8. Borja et al. calculated the maximum possible accommodative amplitude of each measured lens power data point (n=65). As shown, there is good agreement between the age-dependent loss of accommodation and the maximum amplitude of accommodation calculated from the isolated lens power.

Compounds, formulations, and methods are provided that can prevent, reduce, reverse, and/or slow the rate of lens growth, oxidative damage, and/or disulfide bond formation. These compounds, formulations, and methods may thus effectively prevent or treat presbyopia and/or cataract.

The compounds, formulations, and methods described herein employ an active agent that is the choline ester of a reducing agent.

Reducing Agents

The reducing agent is capable of reducing disulfide bonds, particularly disulfide bond formation in lens membranes and membrane associated proteins. Accordingly, particularly preferred reducing agents are capable of entering into the lens epithelial cells.

In one embodiment, the reducing agent enters the lens epithelial cells using a naturally occurring transport mechanism. For example, lipoic acid enters lens cells via specific plasma membrane symporters and antiporters. In one embodiment, the reducing agent is a derivative of lipoic acid that while not structurally identical to lipoic acid, nevertheless maintains the capability of utilizing the naturally occurring transport mechanism for lipoic acid.

In one embodiment, the reducing agent is lipoic acid or a derivative thereof. In some embodiments, the reducing agent is alpha lipoic acid or a derivative thereof. In one embodiment, the reducing agent is lipoic acid per se (5-(1,2-dithiolan-3-yl)pentanoic acid), e.g., alpha lipoic acid.

In another embodiment, the reducing agent is a lipoic acid derivative. Lipoic acid derivatives include, but are not limited to, 6,8-dimercaptooctanoic acid (dihydrolipoic acid) and dihydrolipoate. Lipoic acid derivatives also include selenosubstituted lipoic acid derivatives including, but not limited to, 5-(1,2-thiaselenolan-5-yl)pentanoic acid and 5-(1,2-thiaselenolan-3-yl)pentanoic acid.

In another embodiment, the reducing agent can be any of the reducing agents described in co-pending U.S. patent application Ser. Nos. 11/946,659, 12/267,260, or 12/390,928.

Choline Esters

The reducing agent as described above may be provided as a choline ester. Without being bound by theory, it is believed that the choline ester may improve the agent's solubility in pharmaceutical formulations. It may also improve corneal permeability.

In one embodiment, the active agent is the choline ester of lipoic acid, e.g., alpha lipoic acid, or a lipoic acid derivative. In one embodiment, the active agent is lipoic acid choline ester. In another embodiment, the active agent is alpha lipoic acid choline ester.

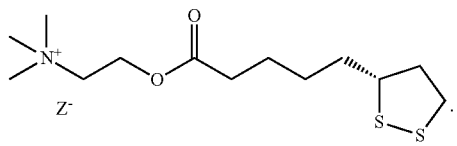 [SMILES: C[N+](C)(C)CCOC(=O)CCCC[C@@H]1CCSS1]

The structure may include a counterion, wherein the counterion is any pharmaceutically acceptable counterion capable of forming a salt. In yet another embodiment, the active agent is the choline ester of a lipoic acid derivative.

Any of the reducing agents can be prepared as a pharmaceutically acceptable salt. The term "pharmaceutically acceptable salt" includes salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mundelic, phthalic, benzenesulfonic, p-tolylsulfonic, citric, tartaric, oxalic, methartesulfonic, and the like. Also included are salts of amino acids such as arginate and the like, and salts of organic acids like glucuronic or galactunoric acids and the like (see, for example, Berge at al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include, but are not limited to, hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In one embodiment, the counterion ion is the 1,3-dihydroxy-2-(hydroxymethyl)propan-2-aminium cation (i.e., a tromethamine salt).

Pharmaceutical Formulations

The active agent can be combined with one or more pharmaceutically acceptable excipients to form a pharmaceutical composition. In the pharmaceutical compositions herein, the active agent may be present as the choline ester.

The active agent can be administered as a racemate or as an enantiomer. Lipoic acid and its derivatives are preferably administered to include the R form. Synthetic methods to yield a racemate may be less expensive than stereo-specific processes including isolation/purification steps. On the other hand, administering a single enantiomer can lower the therapeutically effective, amount, thus decreasing any toxicity effects of the active agent.

As the agents described herein may have therapeutic uses as described in further detail below, it is preferable to select an active agent with low toxicity. Additional acceptable lipoic acid derivatives can be selected by in vitro toxicology testing.

The amount of the active agent (e.g., the reducing agent-choline ester) in the pharmaceutical formulation can be selected based on the condition of the subject to be treated, including the subject's age, gender, as well as vision and lens status. Exemplary amounts of the active agent can be about 0.25% to about 10%, about 0.5% to about 10%, about 1% to about 8%, about 3% to about 7%, about 2% to about 5%, about 5% to about 7%, or about 5%. In another embodiment, the amount of active agent is less than about 0.1% (100 mg) or up to about 10% (10000 mg).

In one embodiment, the pharmaceutical composition is formulated for ocular use. Ocular formulations include, but are not limited to, liquid formulations (e.g., solutions, suspensions) for topical administration as well as formulation for injection or ocular insert administration. Preferably, the ocular formulation is formulated for topical administration such as an eye drop, swab, ointment, gel, or mist (e.g, an aerosol or spray). In one embodiment, the formulation is an eye drop. For ocular formulations, the pharmaceutically acceptable excipients are selected to be compatible with, and suitable for, ocular use. Such excipients are well known in the art. In one embodiment, excipients may be selected to improve the solubility of the agent.

Exemplary excipients include, but are not limited to, buffers, tonicity agents, viscosity agents, preservatives, emulsifiers, salts, lubricants, polymers, solvents, and other known excipients for ocular pharmaceutical formulations. Appropriate amounts can be determined by one of ordinary skill in the art, but non-limiting exemplary amounts (in % by weight) are also provided below.

In one embodiment, the pharmaceutical composition includes one or more buffers to adjust or maintain the pH of the formulation. In one embodiment, the pH is near physiological pH (pH of tears is about 7). Thus, the pH of the formulation can be about 6 to about 8, about 6.5 to about 7.5, about 6.8 to about 7.2, about 7.1 to about 7.5, or about 7. In another embodiment, the pH is about 5.5. Thus, the pH of the formulation can be about 4 to about 7, about 4.5 to about 6, about 4.5 to about 5.5, about 5.5 to about 6.5, about 5 to about 6, about 5.25 to about 5.75, or about 5.5. Exemplary buffers include, but are not limited to, phosphate buffers (e.g., sodium phosphate monobasic monohydrate, sodium phosphate dibasic anhydrous), borate buffers, and HBSS (Hank's Balanced Salt Solution). In one embodiment, the buffer is a phosphate buffer. In another embodiment, the buffer is sodium phosphate monobasic monohydrate and/or sodium phosphate dibasic anhydrous. The buffer amount (amount of either total buffer or a single buffer excipient) can be 0.1% to about 1.0%, about 0.2% to about 0.6%, about 0.05% to about 0.5%, about 0.25% to about 0.45%, or about 0.25%, about 0.43%, or about 0.7%. In one embodiment, the buffer is about 0.05% to about 0.5% (e.g., about 0.27%) sodium phosphate monobasic monohydrate and about 0.2% to about 0.6% (e.g., about 0.43%) sodium phosphate dibasic anhydrous.

In one embodiment, the pharmaceutical composition includes one or more tonicity agents. Although the formulation may be hypertonic or hypotonic, isotonic formulations are preferred (260-320 mOsm). Exemplary tonicity agents include, but are not limited to, sodium chloride. The tonicity agent amount can be about 0.1% to about 5%, about 0.1% to about 2%, about 0.1% to about 1%, about 0.25% to about 0.75%, about 0.2% to about 0.6%, or about 0.5%. In one embodiment, the tonicity agent is about 0.2% to about 0.6% (e.g., about 0.5%) sodium chloride.

In one embodiment the pharmaceutical composition includes one or more viscosity agents to increase the viscosity of the formulation. Exemplary viscosity agents include, but are not limited to, cellulosic agents (e.g., hydroxypropyl methylcellulose), polycarbophil, polyvinyl alcohol. In one embodiment, the viscosity agent is a cellulosic agent, e.g., hydroxypropyl methylcellulose. The viscosity agent amount can be about 0.1% to about 5%, about 0.1% to about 2%, about 0.1% to about 1%, about 0.1% to about 0.4%, or about 0.2%. In one embodiment, the viscosity agent is about 0.1% to about 0.4% (e.g., about 0.2%) hydroxypropyl methylcellulose.

In one embodiment, the pharmaceutical composition includes one or more preservatives to minimize microbial contamination or enhance shelf life. Exemplary preservatives include, but are not limited to, benzalkonium chloride (BAK), cetrimonium, chlorobutanol, edetate disodium (EDTA), polyquaternium-1 (Polyquad®), polyhexamethylene biguanide (PHMB), stabilized oxychloro complex (PURITE®), sodium perborate, and SofZia®. The preservative amount may be, e.g., less than about 0.02%, about 0.004% or less, or about 0.005% to about 0.01%.

In one embodiment, the pharmaceutical composition includes one or more stabilizers. Exemplary stabilizers include, but are not limited to amino acids such as alanine. The stabilizer amount can be about 0.1% to about 5%, about 0.1% to about 2%, about 0.1% to about 1%, about 0.25% to about 0.75%, about 0.2% to about 0.6%, or about 0.5%. In one embodiment, the stabilizer is about 0.2% to about 0.6% (e.g., about 0.5%) alanine.

In one embodiment, the pharmaceutical composition includes one or more emulsifiers. Exemplary emulsifiers include, but are not limited to, Polysorbate 80.

The compounds described herein can be used in combination with one another, with other active agents known to be useful in ocular disease, or with adjunctive agents that may not be effective alone, but may contribute to the efficacy of the active agent. For example, adjunctive agents might include one or more amino acids or choline (separate from the lipoic acid compound) to enhance the efficacy of the active agent. The combinations can be advantageous, e.g., in reducing metabolic degradation.

The term "co-administer" means to administer more than one active agent, such that the duration of physiological effect of one active agent overlaps with the physiological effect of a second active agent. In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Tn some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

Without being bound by theory, it is believed that the administration of an active agent, e.g., lipoic acid or a derivative thereof, and an adjunctive agent such as choline, can be particularly advantageous in a conjugated form. The conjugate compound be applied to the cornea, and penetration is achieved due to the bi-phasic (water and lipid soluble) nature of the conjugate compound. As the conjugate goes through the cornea, naturally present esterases (enzymes) separate lipoic acid from choline. The lipoic acid (now a pro-drug) in the aqueous bathes the lens and enters the lens epithelial cells (due to low molecular weight and size), and there is reduced by any one of several oxido-reductases (enzymes such as thioredoxin and thioltransferase) to form dihydrolipoic acid. Dihydrolipoic acid now has two extra hydrogen atoms to donate to a disulfide complex (e.g., protein disulfide PSSP), separating the two sulfur atoms into sulfhydryl molecules (e.g., protein cysteine residues PSH with free SH groups) thus breaking the inter-cytosol protein cross-links. Breaking these cross-link is what reduces the lens stiffness. Once donation of the hydrogen atoms to the sulfur atom, the dihydrolipoic acid becomes lipoic acid and is available for recycling in the cell to become dihydrolipoic acid or converted to a natural degraded by product thiotactone and excreted.

In one embodiment, a reducing agent, such as one of the compounds described herein, is co-administered with a biochemical energy source. A biochemical energy source facilitates reduction by participating as an intermediate of energy metabolic pathways, particularly the glucose metabolic pathway. Exemplary intermediates of this pathway are depicted by, e.g., Zwingmann, C. et al. 2001. 13C Isotopomer Analysis of Glucose and Alanine Metabolism Reveals Cytosolic Pyruvate Compartmentation as Part of Energy Metabolism in Astrocytes. GLIA 34:200-212. Exemplary biochemical energy sources include, e.g., glucose or a portion thereof (e.g., glucose-6-phosphate (G6P)), pyruvate (e.g., ethyl pyruvate), NADPH, lactate or derivative thereof. G6P may be favored over glucose since a formulation including glucose may further benefit from the addition of preservatives. In one embodiment, the biochemical energy source is an intermediate in a cytosolic metabolic pathway. Exemplary cytosolic pathway intermediates include, e.g., glucose, pyruvate, lactate, alanine, glutamate, and 2-oxoglutarate. In another embodiment, the biochemical energy source is an intermediate in a mitochondrial metabolic pathway. Exemplary mitochondrial pathway intermediates include, e.g., pyruvate, TCA-cycle intermediates, 2-oxoglutarate, and glutamine. In one embodiment, the biochemical energy source is pyruvate compound (e.g., ethyl pyruvate). In another embodiment, the biochemical energy source is alanine. The amount of a biochemical energy source can be, e.g., about 0.05% to about 1.0%. In one embodiment, the energy source is 0.1% ethyl pyruvate.

In one embodiment, the agent is co-administered with glucose-6-phosphate (G6P), NADPH, or glucose. In one embodiment, the agent is activated by an endogenous chemical energy, e.g., endogenous glucose. For example, endogenous glucose can activate lipoic acid or a derivative thereof to dihydrolipoic acid (DHLA) or a corresponding derivative thereof.

In one embodiment, the pharmaceutical formulation includes a reducing agent-choline ester as the active agent and one or more pharmaceutical excipients selected from the group consisting of buffers, tonicity agents, and viscosity agents.

The pharmaceutical formulation may be packaged for administration by any means known in the art including, but not limited to, individual dose units or multi-dose units, e.g., dropper bottles. Multi-dose units may include, for example, about 1 mL to about 100 mL, about 1 mL to about 50 mL, about 1 mL to about 10 mL, about 2 mL to about 7 mL, or about 5 mL. An individual dose may be, e.g., 1-10 drops, 1-5 drops, or 2-3 drops, wherein each drop is about 5 to about 50 µl, about 10 to about 30 µl, or about 20 µl. Depending on the active agent concentration and the condition of the patient, doses may be administered, for example, 1-4, preferably 1-2 times per day.

Methods of Synthesis

Although choline esters may be prepared via a multi-step process as depicted in Example 3, in one embodiment, a one-step method of synthesis for the choline esters is provided. The method comprises: providing a reducing agent as described above, reacting the reducing agent with a halogenated choline to yield a choline ester of the reducing agent. In one embodiment, the halogenated choline is bromocholine bromide as follows:

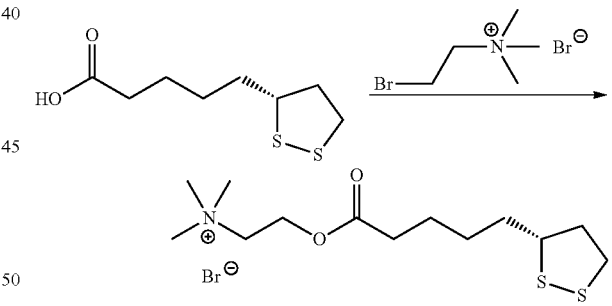

In some embodiments, the reaction is conducted in a solvent, such as acetone or dimethyl formamide (DMF).

In one embodiment, the reaction mixture further includes a base. Exemplary bases include, but are not limited to, $K_2CO_3$, $Cs_2CO_3$, KF, $NaHCO_3$, and $KH_2PO_4$. The base can be present in an amount of about 1 to about 5 equivalents relative to the reducing agent. In some embodiments, the base amount is about 1 eq.

Methods of Treating Oxidation Damage

The agents described herein can be employed in a method including the step of providing a reducing agent-choline ester active agent to a cell, either in vitro or in vivo.

The active agents described herein can be employed in a method for treating or preventing oxidation damage to cells. Such a method includes the step of administering a pharmaceutical composition comprising a reducing agent-choline ester active agent to a cell, either in vitro or in vivo.

As stated above, the agents can be delivered to cells in vitro or in vivo. In one embodiment, the cells are in vivo. In either case, the cells can be ocular cells, e.g., lens cells. In one embodiment, the agent is delivered to a lens, either in vitro or in vivo. In one embodiment, the compounds described herein can be used in a method for treating ocular disease. Exemplary ocular diseases include, but are not limited to: presbyopia, cataract, macular degeneration (including age-related macular degeneration), retinopathies (including diabetic retinopathy), glaucoma, and ocular inflammations. In one embodiment, the ocular disease to be treated is cataract. In another embodiment, the ocular disease to be treated is treat presbyopia. Because oxidative damage has been implicated in other disorders including cancer, the agents may prove useful for administration to any type of cell exhibiting or prone to oxidative damage.

The methods preferably utilize a therapeutically effective amount of the active agent. The term "therapeutically effective amount" means an amount that is capable of preventing, reducing, reversing, and/or slowing the rate of oxidative damage. For ocular applications, a therapeutically effective amount may be determined by measuring clinical outcomes including, but not limited to, the elasticity, stiffness, viscosity, density, or opacity of a lens.

Lens elasticity decreases with age, and is a primary diagnostic and causative factor for presbyopia. Lens elasticity can be measured as accommodative amplitude in diopters (D). FIG. 1 depicts the average elasticity in diopters of an untreated human lens as a function of age in years. The lower the value of D, the less elastic the lens. In one embodiment, the agents described herein (in the active form) can decrease and/or maintain D at a value that is greater than the D value exhibited by an untreated lens of about the same age. In other words, the agents can keep accommodative amplitude "above the line" (the solid line mean accommodative amplitude) depicted in FIG. 1. In one embodiment, D is increased and/or maintained at a value about 2, 5, 7, 10, 15, 25, 50, 100, 150, or 200 percent above the line. However, as individual lenses may differ with respect to average values, another embodiment provides any increase in elasticity, maintenance of elasticity, or reduction in the rate of decline of elasticity (i.e., reduction in the rate of decrease in diopters) for an individual lens compared to the elasticity of the same lens before treatment. In another embodiment, the methods provide an objective increase in elasticity of at least about 0.1, 0.2, 0.5, 1, 1.2, 1.5, 1.8, 2, 2.5, 3, or 5 diopters.

Figure 2:
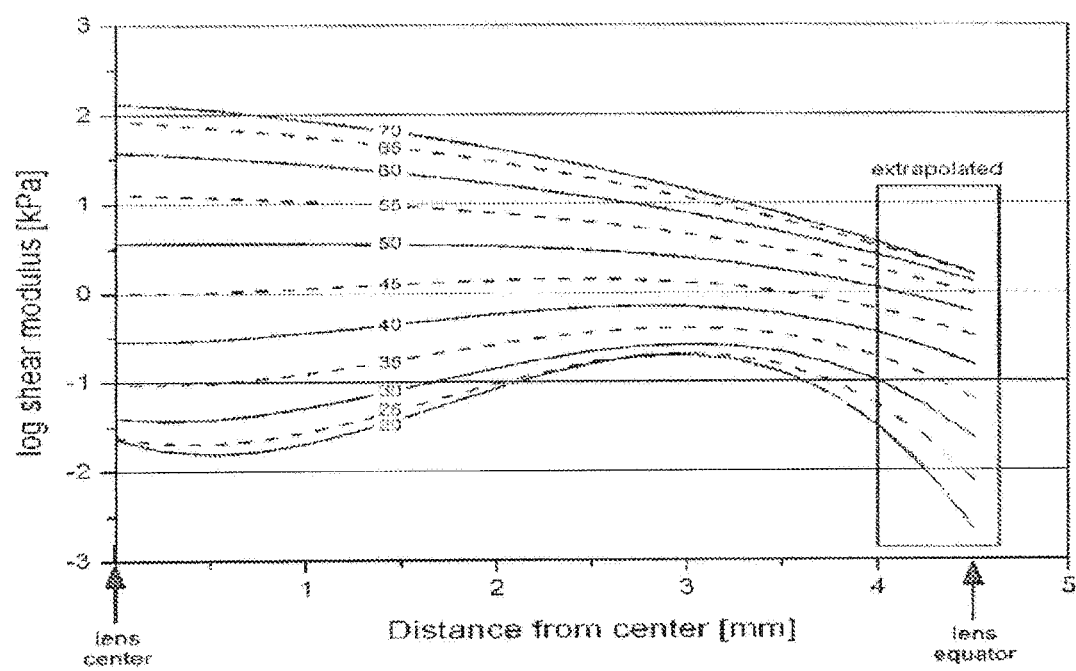
FIG. 2 shows a trend graph of the shear modulus versus position in the lens and age. Weeber, H A et al. 2007. Stiffness gradient in the crystalline lens. Graefes Arch Clin Exp Ophthalmol 245(9):1357-66. The line at the bottom is the 20-year-old lens; the line at the top is the 70-year-old lens. The modulus increases with age for all positions in the lens. Measurements were taken up to 4.0 mm from the lens centre. The lines are extrapolated to a radius of 4.5 mm (lens diameter 9.0 mm).

Lens elasticity can also be measured by the unit of elasticity E. The higher the value of E, the less elastic the lens. FIG. 2 depicts the average elasticity (E) of an untreated human lens as a function of age in years. In one embodiment, the agents described herein (in the active form) can decrease and/or maintain E at a value that is less than the E value exhibited by an untreated lens of about the same age. In other words, the agents can keep lens elasticity "below the line" depicted in FIG. 2. In one embodiment, E is decreased and/or maintained at a value about 2, 5, 7, 10, 15, 25, 50, 100, 150, or 200 percent below the line. However, as individual lenses may differ with respect to average values, another embodiment provides any increase inelasticity, maintenance of elasticity, or reduction in the rate of decline of elasticity (i.e., reduction in the rate of increase in E value) for an individual lens compared to the elasticity of the same lens before treatment.

Figure 3:
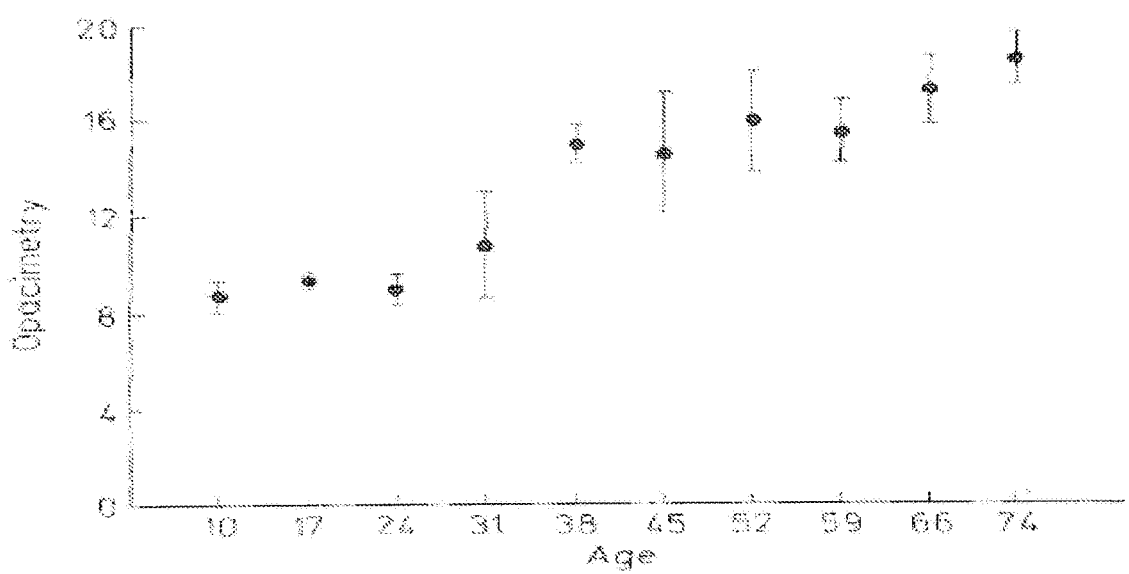
FIG. 3 depicts the average opacity (opacimetry) of an untreated human lens as a function of age in years. Bonomi, L et al. 1990, Evaluation of the 701 interzeag lens opacity meter, Graefe's Arch Clin Exp Ophthalmol 228(5):447-9. Lens opacity was measured in 73 healthy subjects between 10 and 76 years of age without slit-lamp evidence of cataract and with a visual acuity of 20/20. These subjects were classified into ten age groups. This study was carried out using the Interzeag Opacity Meter according to the procedure described by Flammer and Bebies (Flammer J, Bebie H, 1987, Lens Opacity Meter: a new instrument to quantify lens opacity. Ophthalmologica 195(2):69-72) and following the suggestions of the operating manual for the instrument.

Therapeutic efficacy can also be measured in terms of lens opacity. Lens opacity increases with age and is a primary diagnostic and causative factor for cataract. FIG. 3 depicts the average opacity of an untreated human lens as a function of age in years. In one embodiment, the agents described herein (in the active form) can decrease and/or maintain opacity at a value that is less than the opacity value exhibited by an untreated lens of about the same age. In other words, the agents can keep lens opacity "below the line" depicted in FIG. 3. In one embodiment, lens elasticity is decreased and/or maintained at a value about 2, 5, 7, 10, 15, 25, 50, 100, 150, or 200 percent below the line. However, as individual lenses may differ with respect to average values, another embodiment provides any decrease, maintenance, or reduction in the rate of increase of opacity for an individual lens compared to the opacity of the same lens before treatment.

Some agents described herein exist naturally in the untreated eye. Lipoic acid, for example, occurs naturally in eye tissue. In general, a therapeutically effective amount of the exogenously administered agent is often at least about 1 or 2 orders of magnitude larger than the natural level of the compound. In one embodiment, the bioavailable to the lens dose amount of lipoic acid or a derivative thereof is about 5 $\mu$M to about 250 $\mu$M or about 10 $\mu$M to about 700 $\mu$M. The dose amount will depend on the route of administration as well as the age and condition of the patient. Similarly, the frequency of dosing will depend on similar factors as can be determined by one of ordinary skill in the art.

Efficacy has been demonstrated in vitro for specific exemplary dosing. (See Example 2) FIG. 2 shows that the inelasticity increases by a factor of nearly 20 during the critical period from age 40 to 55 years. From current data, a 10 $\mu$M dose can decrease the inelasticity over 95% within a millimeter volume element (voxel). Extrapolation of these results to a volume element in the human lens suggests that using this treatment dose on a 55 year old person with a 10 kPA lens starting modulus value (see FIG. 2) could be reduced after treatment to a value of about 0.5 kPA (which then corresponds to a value typically seen with a 40 yr old person). FIG. 1 permits a conversion of these modulus values to optical amplitude: accommodative amplitude is normally reduced to almost 0 above 55 years, while a person at 40-45 years still exhibits around 4-5 diopters of accommodation.

This method includes the description of a topical ocular formulation that will be used to administer one to two drops of the active agent(s) to the cornea. The formulation will be devised such to provide sufficient active agent and effect treatment to the lens. The mechanism of treatment employs using the intrinsic cellular energy to reduce the active agent lipoate-[S—S] (actually a pro-drug) to dihydrolipoate [DHLA-(SH)$_2$] (the reduced active agent). DHLA is then used to reduce protein disulfide bonds and alter the lens material properties of the lens to restore accommodative amplitude. The activation of the active agent lipoate to DHLA is enzymatically formed with endogenous intracellular oxido-reductase, including such enzymes as thioredoxin, lipoamaide dehydrogenase, and glutathione reductase. These enzymes use endogenous NADPH to affect the redox couple and recycle lipoate to the reduced form: DHLA. DHLA to can however undergo additional metabolism within the lens to produce a number of other products, including 7-(2-mercaptoethyl)thiepan-2-one (henceforth referred to as "DHLA-thiolactone"). A small portion of the DHLA-thiolactone can react with low pK lysine protein residues to form a post-translational acylation product, denoted as Nepsilon-lipoyl group. This later post-translation product is normally localized in the mitochondrial system and is important with the pyruvate dehydrogenase-acetyltansferase activity. Any excess DHLA-thiolactone is released into the aqueous along with DHLA itself and other byproducts. At 15 minutes to 2 hours after topical dosing, the amount of DHLA-thilolactone measured in the aqueous ranges from 10 micro molar levels to 700 micro molar levels.

The methods include preventative methods that can be performed on patients of any age. The methods also include therapeutic methods that can be performed on patients of any age, particularly patients that are 20, 25, 30, 35, 40, 45, 50, 52, 55, 57, 60, 70, 75, or 80 years of age or older.

Any numerical values recited herein include all values from the lower value to the upper value in increments of any measurable degree of precision. For example, if the value of a variable such as age, amount, time, percent increase/decrease and the like is 1 to 90, specifically from 20 to 80, and more specifically from 30 to 70, it is intended that values such as 15 to 85, 22 to 68, 43 to 51, 30.3 to 32, etc., are expressly enumerated in this specification. In other words, all possible combinations of numerical values between the lowest value and the highest value enumerated are to be considered to be expressly stated in this application in a similar manner.

EXAMPLES

Example 1

In vitro Toxicology Studies

Cell viability was determined using human umbilical vein endothelial cells (HUVEC, first passage). Cells were treated with the active agent in doses ranging from 0.1 µM to 100 µM. The number of live and dead cells was determined using the MultiTox-Fluor assay (Promega) or Live/Dead® assay (Invitrogen). Logistic plots were used to determine the compound's $LD_{50}$ value. Lipoic acid was not cytotoxic the concentration range.

Example 2

In vitro Efficacy Studies

Increase in Elasticity: Pairs of mouse lenses were incubated in medium 200 supplemented with an antibiotic, an antimycotic, the presence or absence of lipoic acid (concentrations ranging from 0.5 µM to 500 µM) for 8-15 hours. Each lens was removed from medium, weighed, and photographed on a micrometer scale. A coverslip of known weight (0.17899±0.00200 g) was placed on the lens, and the lens was photographed again on the micrometer scale. The diameter of each lens with and without the coverslip was determined from the photographs. The change in lens diameter produced by the force (coverslip) was computed $\Delta D=(D_{withcoverslip}-D_{withoutcoverslip})$. The results (FIG. 4, ‡) indicate that lipoic acid at concentrations ≥9.6 µM caused a statistically significant increase in $\Delta D$, p<0.0001.

Figure 4:
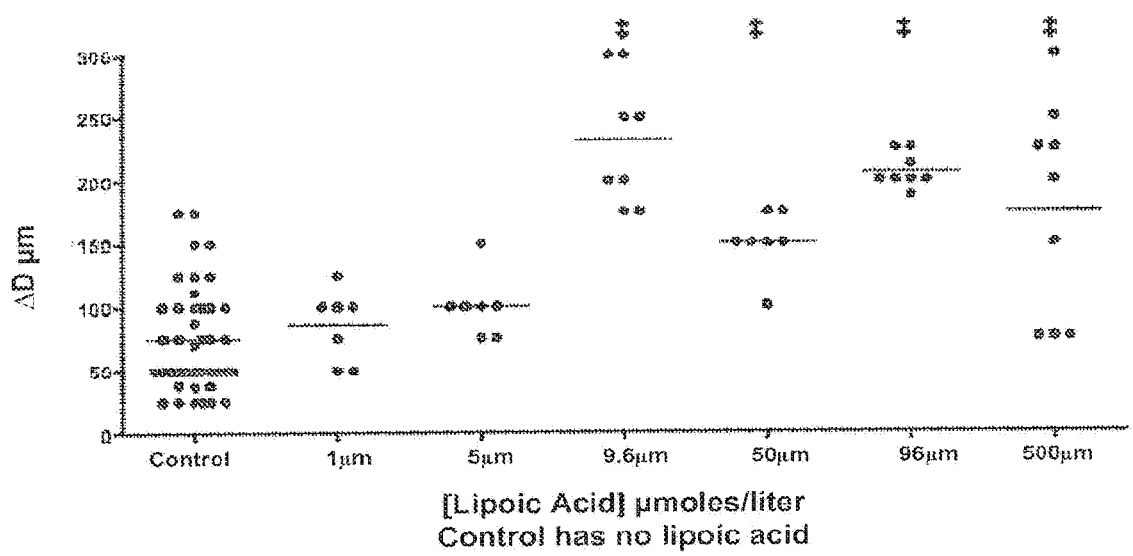
FIG. 4 depicts a scatter plot of the change in ΔD (micrometers) in the absence (control) and presence of lipoic acid in lens organ culture experiments. The symbol ‡ designates significantly larger changes in ΔD when compared to controls. Statistical values are highly significant at p<0.0001 by unpaired t-test and by Kruskal Wallis test, which compared medians of each data set. The relative change in Young's modulus (E) can be calculated as the cubic value derived from the ΔD of the control divided by the ΔD of the experimental or E fractional change=(ΔD con/ΔDexp)^3.
Figure 5:
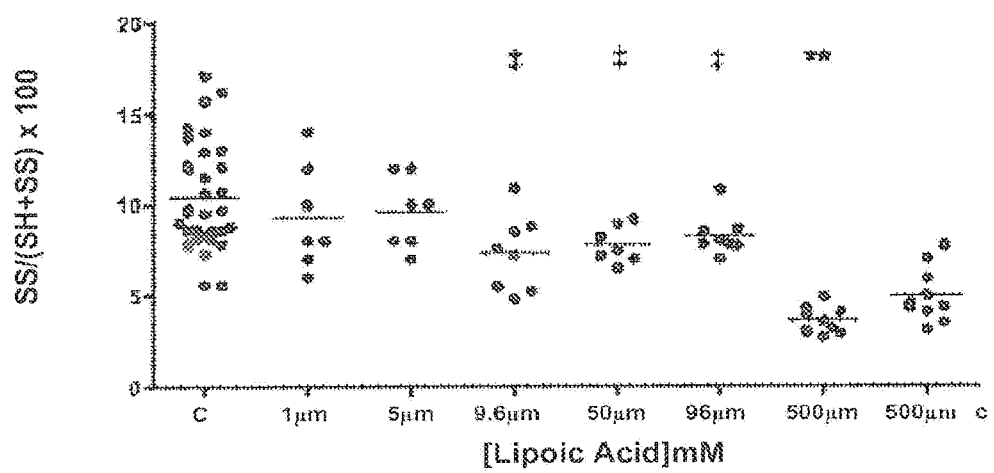
FIG. 5 depicts a scattergram of the percent of the total protein SH groups in disulfide bonds. Free SH groups were alkylated with 4-acetamido-4'-maleimidylstilbene-2,2'-sulfonic acid (c, 1 μM, 5 μM, 9.6 μM, 50 μM, 96 μM) or 7-diethylamino-3-(4'maleimidylphenyl)-4-methyl coumarin (500 μM, and 500 μM c). Following removal of the first alkylating agent, the S—S bonds were reduced and alkylated with fluorescein-5-maleimide. Absorption spectra were used to calculated total protein (A280 nm), free protein SH (A322 or A384), and protein SS (A490) using the appropriate extinction coefficients. The symbol ‡ indicates statistically significant difference of mean with mean of control (c, p≤0.05). The symbol ** indicates means of 500 μM lipoic acid and the 500 μM control were significantly different from each other (p=0.027).

Decrease in disulfide bonds: Lipoic acid at concentrations ≥9.6 µM caused a statistically significant decrease in protein disulfides in the mouse lenses where there was a significant increase in $\Delta D$ (FIG. 4). Mouse lenses were homogenized in a denaturing buffer containing a fluorescent alkylating agent to modify the free SH groups. After removing the alkylating agent homogenates were reduced and alkylated with a different fluorescent alkylating agent. Absorption spectra of the modified proteins were used to calculate free protein SH and protein SS groups. The results are shown in FIG. 5.

Example 3

Syntheses of Lipoic Acid Choline Ester

Lipoic acid choline ester was prepared according to the following synthetic route. Choline salts of alternative reducing agents can be similarly prepared by making the appropriate reagents substitutions. Also, one of ordinary skill in the art would recognize that these syntheses are provided as guidance and that reagents, conditions, amounts, temperatures, and the like may be modified without departing from the general synthetic pathway.

Step 1:

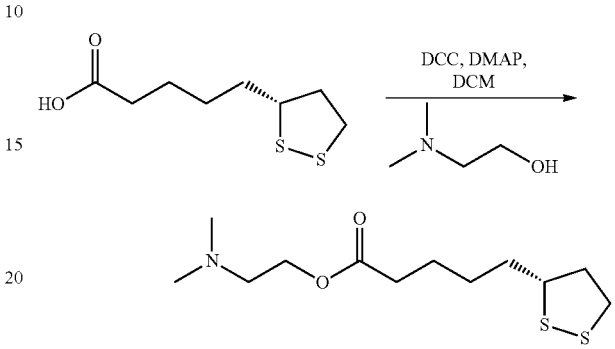

(R)-2-(dimethylamino)ethyl 5-(1,2-dithiolan-3-yl)pentanoate. A solution of DCC (11 g, 53 mmol) in anhydrous $CH_2Cl_2$ (20 mL) was added with stirring over 10-20 minutes to a cold (0° C.) solution of R-lipoic acid (10.0 g, 48.5 mmol), N,N-dimethylethanolamine (14.5 mL, 145 mmol, 3 eq.), and DMAP (600 mg, 4.9 mmol) in anhydrous $CH_2Cl_2$ (50 mL). Following complete addition, the cold bath was removed. After 18 hours at room temperature, all volatiles were removed under reduced pressure, and the resulting residue was purified by flash column chromatography ($SiO_2$, 2% MeOH in $CH_2Cl_2$) providing the desired product as a clear yellow oil (10.6 g, 79%). All data consistent with values reported in the literature. (See Courvoisier C. et al. 2006. Synthesis and effects of 3-methylthiopropanoyl thiolesters of lipoic acid, methional metabolite mimics. Bioorganic Chemistry 34(1):49-58.)

Step 2:

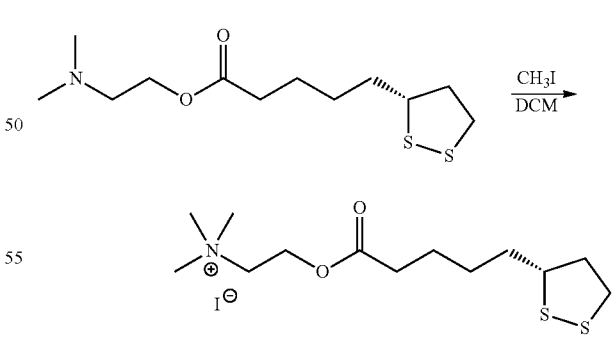

(R)-2-(5-(1,2-dithiolan-3-yl)pentanoyloxy)-N,N,N-(trimethyl)ethylammonium iodide. Methyl iodide (0.55 mL, 9.0 mmol) was added to a solution of the amine (2.5 g, 9.0 mmol) in anhydrous $CH_2Cl_2$ (20 mL). The reaction mixture was stirred overnight and slowly poured into diethyl ether (250 mL) with vigorous stirring. The choline salt was isolated by filtration as a free-flowing pale, yellow sold (3.7 g, 98%).

Example 4

One-Step Synthetic Route

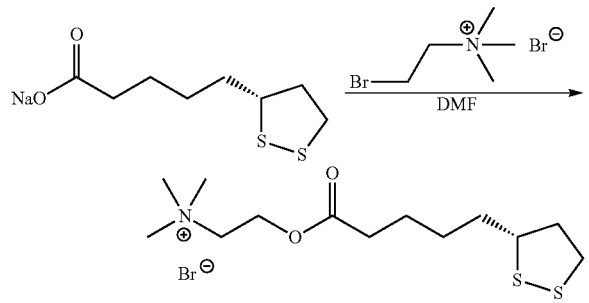

Example 5

Eye Drop Formulation of Lipoic Acid Choline Ester

The following eye drop formulation was prepared using lipoic acid choline ester as the active agent.

Formula A

| Ingredient | Concentration % by weight | Purpose |
|---|---|---|
| Lipoic acid choline ester | 5.0 | Active agent |
| Ethyl pyruvate | 0.1 | Energy source |
| Sodium phosphate monobasic monohydrate, USP | 0.269 | Buffer |
| Sodium phosphate dibasic anhydrous, USP | 0.433 | Buffer |
| Sodium chloride | 0.5 | Tonicity agent |
| Hydroxypropylmethylcellulose (HPMC), USP | 0.2 | Viscosity agent |
| De-ionized, pyrogen free water | to 100 mL | Solvent |

Formula B

| Ingredient | Concentration % by wieght | Purpose |
|---|---|---|
| Lipoic acid choline ester | 5.0 | Active agent |
| Alanine | 0.5 | Stabilizer |
| Sodium phosphate monobasic monohydrate, USP | 0.269 | Buffer |
| Sodium phosphate dibasic anhydrous, USP | 0.433 | Buffer |
| Sodium chloride | 0.5 | Tonicity agent |
| Hydroxypropylmethylcellulose (HPMC), USP | 0.2 | Viscosity agent |
| De-ionized, pyrogen free water | to 100 mL | Solvent |

The eye drop formulation has a pH of 7.0.

The pharmaceutical formulation may be diluted to 100 ml filtered water (e.g., Millex syringe filter (0.45 micron 33 mm). The pharmaceutical composition may be packaged for multi-dose administration, e.g., 2-7 mL (e.g., 5 mL) eyedropper bottle with screw lid dropper.

The examples given above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes of carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

What is claimed is:

1. A pharmaceutical composition comprising an active agent that is a reducing agent-choline ester and at least one pharmaceutically acceptable excipient, wherein the reducing agent is a dithiol compound or a dithiol derivative.

2. The pharmaceutical composition of claim 1, wherein the reducing agent is a compound having a formula:

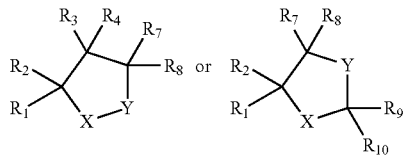

wherein at least one of X and Y is sulfur, and the other is sulfur, selenium, or a sulfonic group, and each R group is independently selected from the group consisting of: —H, —OH, —OAc, —OR, —SR, —$CO_2R$, an electron withdrawing group, and a linear or branched $C_{1-18}$ is alkane or alkene optionally substituted by one or more substituents selected from the group consisting of ether, ester, carboxylic acid, phosphate, amide, and amine groups.

3. The pharmaceutical composition of claim 1, wherein the reducing agent is a compound having a formula:

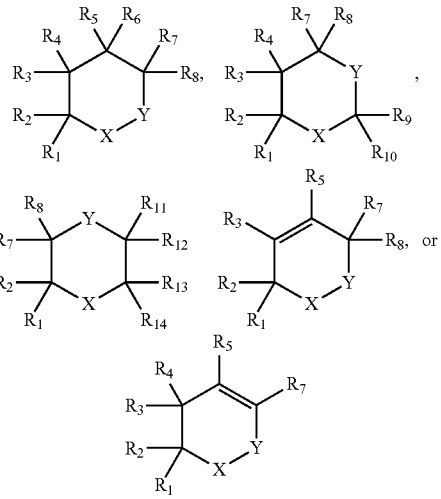

wherein at least one of X and Y is sulfur, and the other is sulfur, selenium, or a sulfonic group, and each R group is independently selected from the group consisting of: —H, —OH, —OAc, —OR, —SR, —$CO_2R$, an electron withdrawing group, and a linear or branched $C_{1-18}$ is alkane or alkene optionally substituted by one or more substituents selected from the group consisting of ether, ester, carboxylic acid, phosphate, amide, and amine groups.

4. The pharmaceutical composition of claim 1, wherein the reducing agent is a compound having a formula:

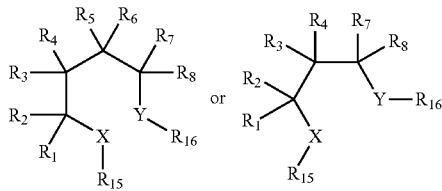

wherein at least one of X and Y is sulfur, and the other is sulfur, selenium, or a sulfonic group, and wherein each R group is independently selected from the group consisting of: —H, —OH, —OAc, —OR, —SR, —$CO_2R$, an electron withdrawing group, and a linear or branched $C_{1-18}$ alkane or alkene optionally substituted by one or more substituents selected from the group consisting of ether, ester, carboxylic acid, phosphate, amide, and amine groups.

5. The pharmaceutical composition of claim 1, wherein the reducing agent is a compound having a formula:

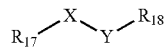

wherein at least one of X and Y is sulfur, and the other is sulfur, selenium, or a sulfonic group, and each R group is independently selected from the group consisting of —H, —OH, —OAc, —OR, —SR, —$CO_2R$, an electron withdrawing group, and a linear or branched $C_{1-18}$ alkane or alkene optionally substituted by one or more substituents selected from the group consisting of ether, ester, carboxylic acid, phosphate, amide, and amine groups.

6. The pharmaceutical composition of claim 1, formulated for topical ocular delivery.

7. The pharmaceutical composition of claim 1, wherein the composition is an eye drop.

8. The pharmaceutical composition of claim 1, comprising a biochemical energy source.

9. The pharmaceutical composition of claim 8, wherein the biochemical energy source is alanine, or a pyruvate or derivative thereof.

10. A method of treating or preventing an ocular disease, comprising administering to a subject the pharmaceutical composition of claim 1.

11. The method of claim 10, wherein the pharmaceutical composition is administered topically.

12. The method of claim 10, wherein the ocular disease is presbyopia.

* * * * *